US011826272B2

(12) United States Patent
Grange (10) Patent No.: US 11,826,272 B2
(45) Date of Patent: Nov. 28, 2023

(54) HAND ORTHOSIS FOR SUPPORTING THE THUMB IN PARTICULAR IN CASE OF RHIZARTHROSIS (71) Applicant: MILLET INNOVATION, Loriol sur Drome (FR)

(72) Inventor: Odile Grange, Allex (FR)

(73) Assignee: MILLET INNOVATION, Loriol sur Drome (FR)

(*) Notice: Subject to any disclaimer, the term of this patent is extended or adjusted under 35 U.S.C. 154(b) by 542 days.

(21) Appl. No.: 14/914,111

(22) PCT Filed: Jul. 30, 2014

(86) PCT No.: PCT/FR2014/051980
§ 371 (c)(1),
(2) Date: Feb. 24, 2016

(87) PCT Pub. No.: WO2015/028734
PCT Pub. Date: Mar. 5, 2015

(65) Prior Publication Data
US 2016/0206464 A1 Jul. 21, 2016

(30) Foreign Application Priority Data
Sep. 2, 2013 (FR) ...................................... 13 58389

(51) Int. Cl.
*A61F 5/01* (2006.01)
*A61F 5/30* (2006.01)
*A61F 5/34* (2006.01)

(52) U.S. Cl.
CPC .............. *A61F 5/0118* (2013.01); *A61F 5/30* (2013.01); *A61F 5/34* (2013.01)

(58) Field of Classification Search
CPC .. A61F 5/0118; A61F 5/30; A61F 5/34; A61F 5/0104; A61F 5/01; A61F 5/05866;
(Continued)

(56) References Cited

U.S. PATENT DOCUMENTS 1,471,948 A * 10/1923 Cox .................... A61F 5/05866
602/22
4,964,402 A * 10/1990 Grim .................... A61F 5/0111
602/2
(Continued)

FOREIGN PATENT DOCUMENTS

DE  4103383 A1  8/1992
FR  2822371 A1  9/2002
(Continued)

OTHER PUBLICATIONS

Merriam-Webster Dictionary; "elastic," https://www.merriam-webster.com/dictionary/elastic.*
(Continued)

*Primary Examiner* — Victoria Hicks Fisher
(74) *Attorney, Agent, or Firm* — Oliff PLC (57) ABSTRACT A hand orthosis for supporting the thumb including a main part including: a first portion in the form of a sleeve fitted to a portion of the thumb extending to the fold area between the thumb and the palm of the hand, a second portion assembled by a seam line formed as a sleeve fitted to the wrist, a third portion linking the first and second portions, shaped to envelop an area of the hand extending along the thumb metacarpal between the back and the palm of the hand, and including an opening to allow the palm of the hand to pass therethrough, the main part shaped not to cover the fold area between the thumb and the palm of the hand and being made from an elastic material having a Young's modulus of between 0.5 Mpa and 1 Mpa in a direction corresponding to a longitudinal axis of the first portion.

18 Claims, 5 Drawing Sheets (58) Field of Classification Search
CPC .. A61F 5/05858; A61F 5/05841; A61F 5/058; A61F 5/05875; A61F 5/05
See application file for complete search history.

(56) References Cited

U.S. PATENT DOCUMENTS

| | | | |
|---|---|---|---|
| 4,964,405 A * | 10/1990 | Arnoth | A62B 7/10 128/205.12 |
| 6,702,772 B1 | 3/2004 | Colditz | |
| 6,845,514 B1 * | 1/2005 | Yao | A61F 13/104 128/878 |
| 2003/0191421 A1 | 10/2003 | Weaver et al. | |
| 2008/0249446 A1 * | 10/2008 | Baumgartner | A61F 5/05866 602/7 |
| 2012/0316485 A1 * | 12/2012 | Fryda | A61F 5/0118 602/21 |
| 2013/0116608 A1 * | 5/2013 | Romcevich | A61F 5/0104 602/1 |

FOREIGN PATENT DOCUMENTS

| | | |
|---|---|---|
| FR | 2892298 A1 | 4/2007 |
| WO | 2013/001083 A1 | 1/2013 |

OTHER PUBLICATIONS

"Material Data Book," Jan. 1, 2013, Retrieved from the internet: URL: www.- mdp.eng.cam.ac.uk, p. 11.
Jan. 4, 2015 Search Report issued in International Patent Application No. PCT/FR2014/051980.

\* cited by examiner

HAND ORTHOSIS FOR SUPPORTING THE THUMB IN PARTICULAR IN CASE OF RHIZARTHROSIS

The present invention relates to a thumb orthosis. The present invention aims in particular to relieve people suffering from rhizarthrosis.

With age, a great many people suffer from arthrosis, in particular at the joint between the thumb and the wrist. This ailment, called "rhizarthrosis", particularly affects women and manifests itself by sudden sharp pains. At night, random movements of the thumb may cause pain to the point of preventing sleep. This ailment may concern the joint between the trapezium and the metacarpus of the thumb and/or the joint between the scaphoid bone and the trapezium and the trapezoid. This ailment may also result in an instability or a subluxation of the joint between the trapezium and the metacarpus of the thumb.

Rhizarthrosis is generally treated with drugs and/or orthopedic accessories. Some of these accessories come in the form of rigid orthoses aiming to totally immobilize the joint in question. Therefore, these orthoses are mainly worn at night. By immobilizing the joint, they remove the pain when the joint is causing suffering. They also avoid a certain fatigue of the joint by preventing involuntary movements.

The main disadvantage of these orthoses lies in their rigidity which prevents normal use of the thumb and in particular of the essential function of the hand, i.e. the gripping function. These orthoses also have the disadvantage of having to be custom-made, for example by thermoforming them on the hand.

Elastic orthoses also exist and also aim to immobilize the joint. However, the hand's gripping function significantly increases the stresses in the articular chain between the thumb and the wrist. Thus, the force exerted by the grip is multiplied by twelve on the carpometacarpal joint. The result is that these orthoses must apply a high compression value at the base of the wrist, particularly to contain movements related to a possible subluxation of the joint. Therefore, these orthoses must also be custom-made.

Furthermore, orthoses exist in the form of a gauntlet glove, also custom-made by thermoforming them on the hand. All the orthoses described above have the disadvantages not only of having to be custom-made, but also of covering the fold between the thumb and the palm. The result is that only the interphalangeal joint, of the thumb is not blocked.

It is thus desirable to produce a thumb orthosis capable of relieving the carpometacarpal joint, but without hindering the gripping function of the hand. It is also desirable to produce a thumb orthosis that does not need to be custom-made, but only in a few standard sizes, without requiring any final adjustment.

Some embodiments relate to a hand orthosis for supporting the thumb, the orthosis comprising a main part comprising: a first portion in the form of a sleeve fitted to a portion of the thumb extending to the fold area between the thumb and the palm of the hand, a second portion in the form of a sleeve fitted to the wrist, and a third portion linking the first and second portions, shaped to envelop an area of the hand extending along the thumb metacarpal between the back and the palm of the hand, and comprising an opening to allow the palm of the hand to pass therethrough. According to one embodiment, the second portion is assembled by a seam line to take the form of a sleeve, and the main part is shaped so as not to cover the fold area between the thumb and the palm of the hand and is made from an elastic material having a Young's modulus of between 0.5 Mpa and 1 Mpa in a direction corresponding to a longitudinal axis of the first portion.

According to one embodiment, the first portion is shaped to cover the joint between the two phalanges of the thumb.

According to one embodiment, the main part comprises two layers of elastic fabric assembled by adhesion.

According to one embodiment, each of the two layers is made from a fabric comprising between 75 and 85% by weight of polyamide and between 15 and 25% by weight of elastane.

According to one embodiment, each of the two layers has a weight per unit area of 155 g/m2, and/or a thickness of between 0.5 and 0.7 mm.

According to one embodiment, each of the two layers has an elasticity of 85% to 115% in the direction of the warp and of 65% to 95% in the direction of the weft.

According to one embodiment, the orthosis comprises a pad made from a material capable of performing a cushioning function, the pad being set inside the second and third portions in an area covering the joint between the metacarpal of the thumb and the wrist.

According to one embodiment, the pad is made from a cross-linked polymer gel.

According to one embodiment, the pad has a thickness of between 0.4 and 1 mm.

According to one embodiment, the pad is adhered onto an overlapping part made from an elastic fabric that is assembled with the main part by a seam, such that the pad is sandwiched between the main part and the overlapping part.

According to one embodiment, the pad is sewn with the overlapping part onto the main part.

According to one embodiment, the main part is fitted to the hand and to the thumb to support the joints of the thumb in a hand configuration in which all the hand muscles are relaxed and in which no external forces are exerted on the joints of the thumb.

According to one embodiment, the main part is made from a material having a thickness of between 1 mm and 1.4 mm.

Some examples of embodiments of the present invention will be described below in relation with, but not limited to, the accompanying figures, in which.

Figure 1A:
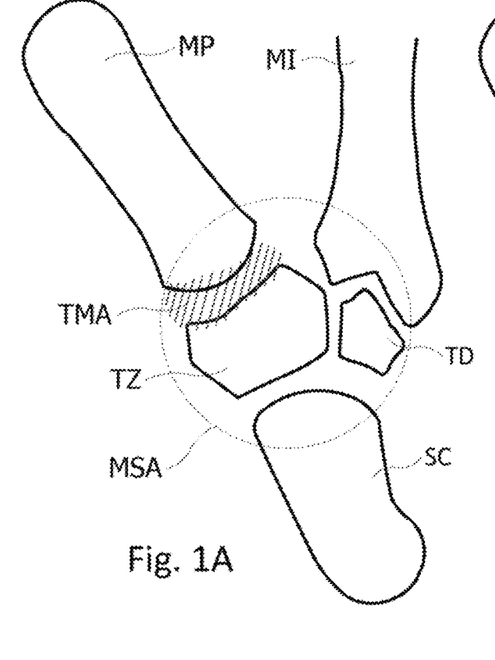
FIGS. 1A, 1B, 1C schematically represent the carpometacarpal joints of the thumb, suffering from different ailments that could be relieved by the orthosis according to the present invention.
Figure 1B:
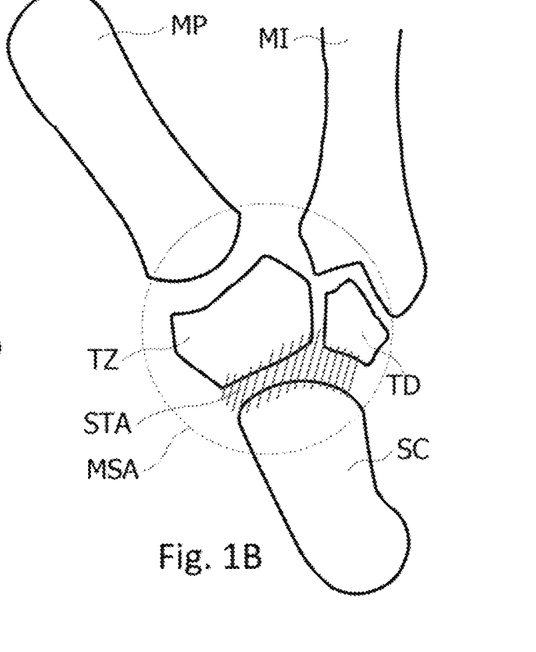
Figure 1C:
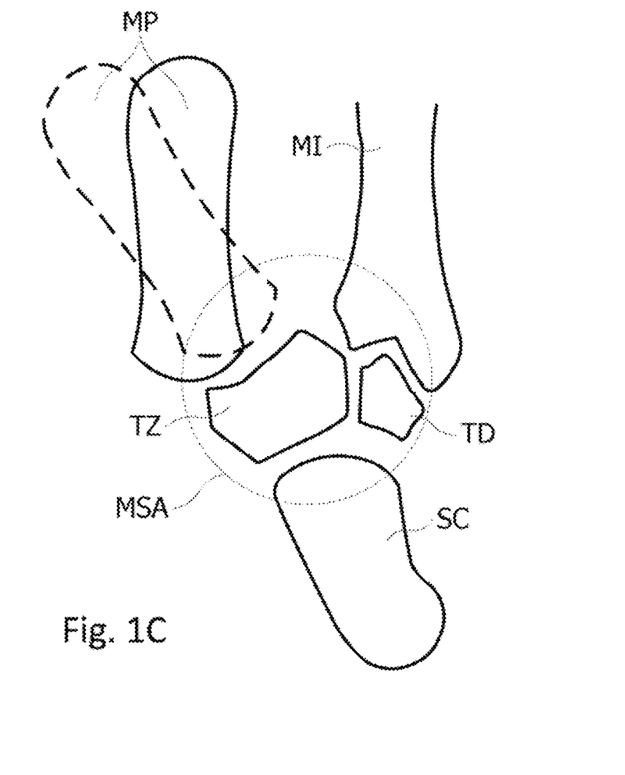

FIGS. 1A, 1B, 1C represent the carpometacarpal joints of the thumb and of the forefinger. The carpometacarpal joints of the thumb MSA comprise a joint between the metacarpus MP and the trapezium TZ, and a joint between the scaphoid bone SC on the one hand, and the trapezium TZ and the trapezoid TD on the other. The carpometacarpal joints of the forefinger comprise a joint between the metacarpus MI of the forefinger and the trapezoid TD and a joint between the trapezoid TD and the scaphoid bone SC. The arthrosis may affect one and/or the other joint MSA, identified by hatching on FIGS. 1A and 1B. The thumb can also be affected by a subluxation of the metacarpus MP in relation to the trapezium TZ, as shown in FIG. 1C.

Figure 2:
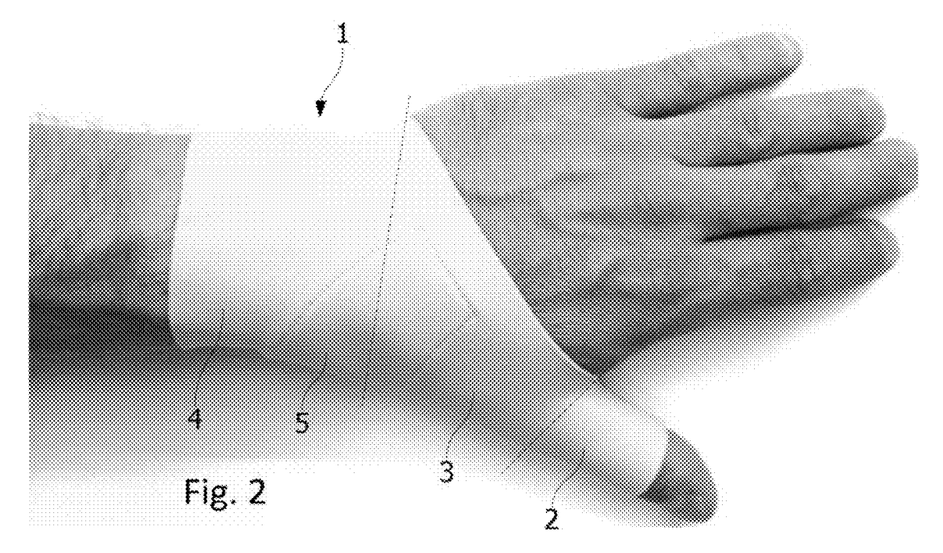
FIG. 2 represents the back face of a hand fitted with an orthosis according to one embodiment.
Figure 3:
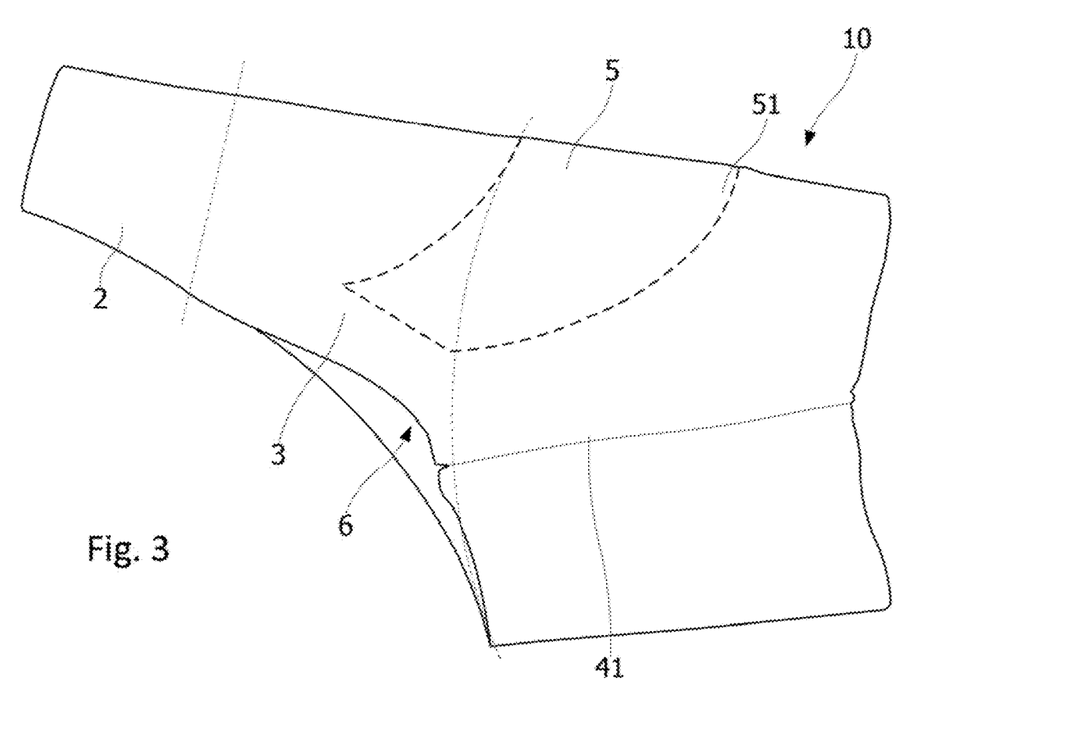
FIG. 3 represents a portion of the outer face of the orthosis.
Figure 4:
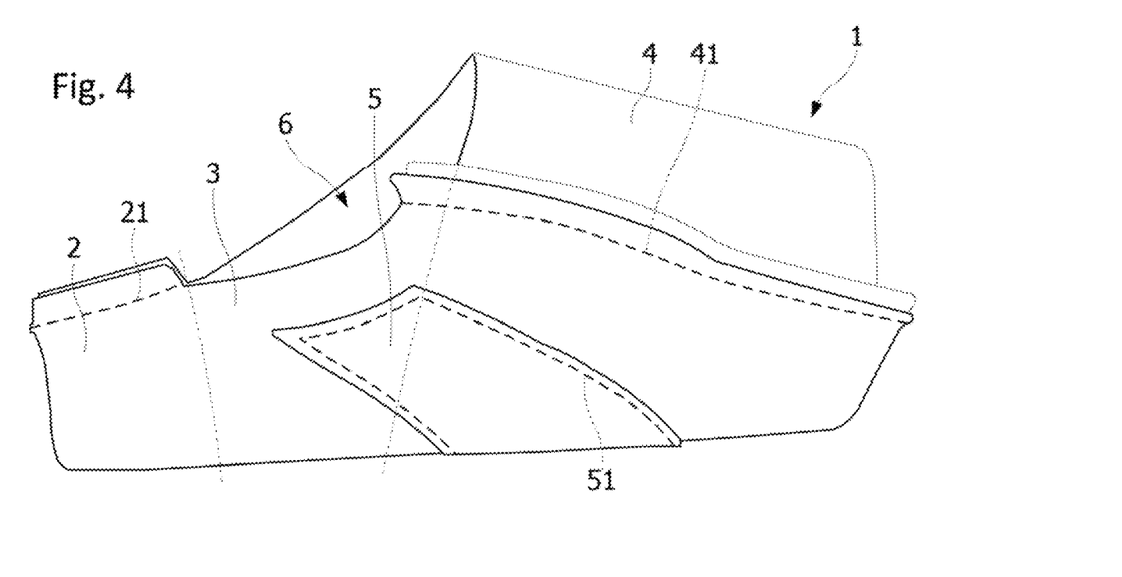
FIG. 4 represents a portion of the inner face of the orthosis in a configuration turned inside out.
Figure 6:
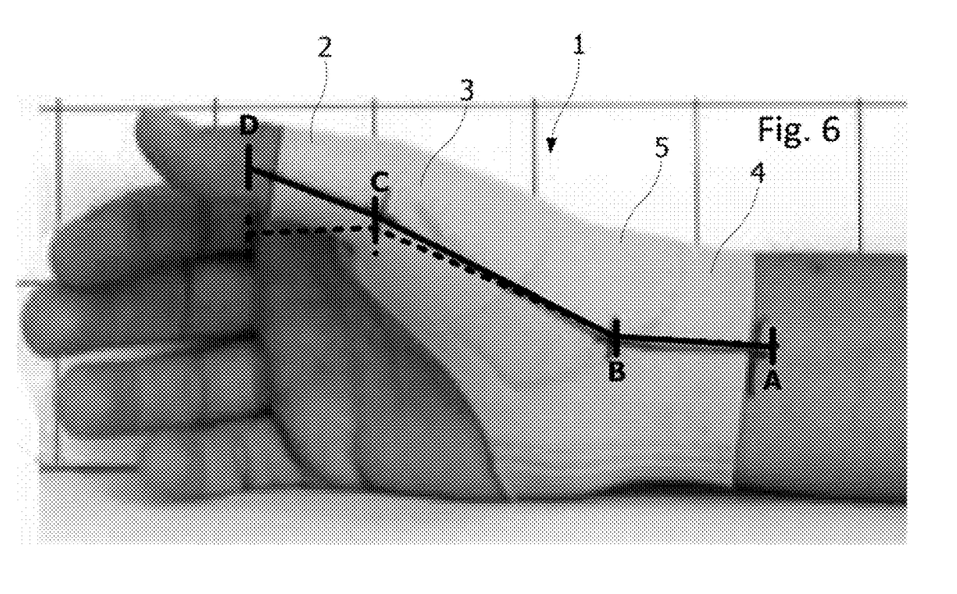
FIG. 6 represents the inner face of the hand in the configuration presented on FIG. 5, fitted with the orthosis of FIGS. 2 to 4.

FIGS. 2 to 4 and 6 represent a thumb orthosis, according to one embodiment, aiming to relieve people suffering from rhizarthrosis or a subluxation of the metacarpus of the thumb. FIGS. 2 and 6 represent the orthosis placed on a hand. FIGS. 3 and 4 respectively represent a portion of the outer face and of the inner face of the orthosis. The orthosis comprises a main part or sleeve 1 comprising a distal portion 2, a proximal portion 4, and an intermediate portion 3 linking the portions 2 and 4, delimited on FIGS. 2 to 4 by lines made up of dots and dashes. The portion 2 in the form of a sleeve is shaped to cover and support the thumb from the fold area between the thumb and the palm of the hand, to the interphalangeal joint of the thumb. The portion 2 may extend for example to the vicinity of the middle of the distal phalanx of the thumb. The portion 4, also in the form of a sleeve, is shaped to cover a portion of the forearm, the wrist, the carpometacarpal joints of the thumb, and a proximal portion of the finger metacarpuses. The intermediate portion 3 has an opening 6 extending between the portions 2 and 3, to allow the palm of the hand to pass therethrough.

The main part 1 is made from an elastic material and fitted to the shape of the hand and of the thumb to be supported, without exerting thereon any excessively intense restraining force, susceptible of causing pain, in particular in the sensitive zone of the carpometacarpal joints MSA. The orthosis may be easily removed in the direction of the end of the fingers and the thumb, in particular due to the absence of any areas of constriction. In some embodiments, the hand orthosis is exclusively made of elastic material.

According to one embodiment, the material forming the part 1 has a certain rigidity which combines with a beam effect conferred by the tubular or semi-tubular curved cross section shape of the orthosis. The rigidity resulting from the material and from the beam effect renders the orthosis susceptible of bearing the weight of the thumb without bending.

According to one embodiment, the material forming the part 1 has a Young's modulus of between 0.5 MPa and 1 MPa, for example substantially equal to 0.7 MPa. The beam effect obtained can be characterized by the second moment of area. This moment is approximately 3,000 mm4 for the thumb sleeve 2, and approximately half for the intermediate portion 3.

Figure 5:
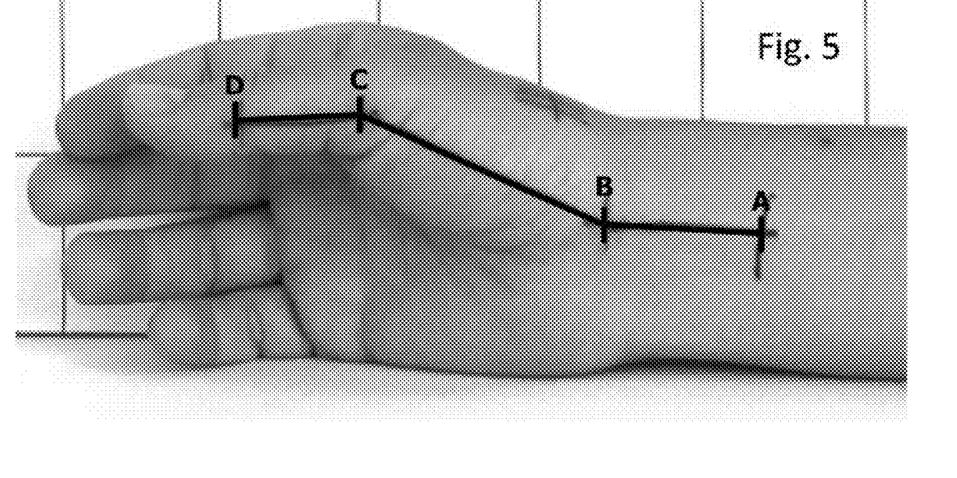
FIG. 5 represents the inner face of a hand in a configuration placed on its side, muscles relaxed.

The ability of the orthosis to bear the weight of the thumb is, shown by FIGS. 5 and 6. FIGS. 5 and 6 represent the inner face of a hand placed on its side on a horizontal plane, the hand muscles relaxed. The axes of the forearm, of the metacarpus of the thumb and of the proximal phalanx of the thumb are respectively identified by segments [A,B], [B,C] and [C,D]. The carpometacarpal MSA and metacarpophalangeal joints of the thumb are identified by points B and C. In the configuration of the hand shown on FIG. 5, it appears that the joints B and C are flexed under the effect of the weight of the thumb. The thumb is thus substantially below the level of the forefinger of the hand on FIG. 5. On FIG. 6, the hand is in the same configuration as on FIG. 5, but is fitted with the orthosis. It can be seen on FIG. 6 that the thumb is at a level above the forefinger of the hand. According to the configuration of segments [B,C] and [C,D] on FIG. 5 reproduced in dotted lines on FIG. 6, the angle ABC appears slightly smaller on FIG. 6 than on FIG. 5. The angle BCD appears substantially larger (by about twenty degrees) on FIG. 6 than on FIG. 5.

Thanks to the rigidity of the orthosis, the joints B and C of the thumb do not undergo any involuntary movements, for example upon changes in the direction of the hand in relation to gravity or in connection with kinematics. This rigidity also enables the amplitude and the duration of involuntary movements such as reflexes to be reduced. However, the elasticity of the material forming the part 1 means the orthosis does not hinder voluntary thumb movements, and thus avoids significant additional efforts having to be made on the troubled joint during such voluntary movements. The user may thus hold an object with his hand by exerting a minimum additional effort to offset the stiffness of the orthosis. It shall be noted on FIGS. 2 and 6 that the orthosis does not cover the fold area between the thumb and the palm of the hand and thus does not hinder the gripping function of the hand. It shall also be noted that the support effect conferred by the orthosis extends to the metacarpophalangeal joint C of the thumb, as this joint may also suffer from arthrosis.

According to one embodiment, the material in which the part 1 is formed is produced using two layers of an elastic fabric, adhered onto each other, by a layer of glue of an approximate thickness of 0.05 mm. The layer of glue can be uniformly distributed between the two layers of fabric, or disposed in uniformly distributed dots. The two layers of fabric can be adhered to each other by coating one of the two layers with glue, and by pressing the two layers against each other, by means of one or two rollers.

The fabric forming the two layers may be a fabric made of polyamide (approximately 80% by weight) and elastane (approximately 20% by weight), having a weight per unit area of 155 g/m2. The glue used may be polyurethane based. The material assembly formed by the two thicknesses of fabric and the layer of glue may have a weight per unit area of 355 g/m2. The fabric forming the two layers may have a thickness of between 0.5 and 0.7 mm. The result is that the material in which the part 1 is formed may have a thickness between 1 and 1.4 mm. This fabric may have an elasticity of between 85% and 115% in the direction of the warp and between 65% and 95% in the direction of the weft.

Figure 8:
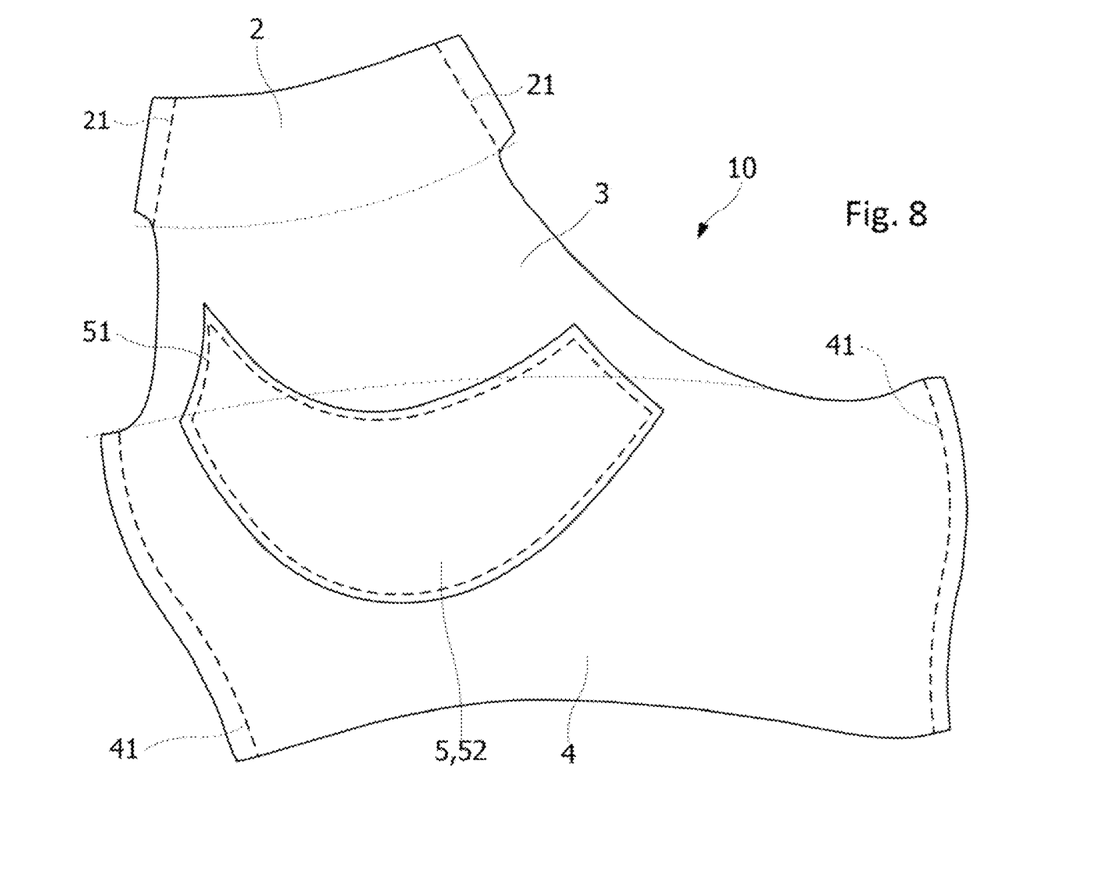
FIG. 8 represents the shape of a piece laid flat from which the orthosis can be made, according to one embodiment.

According to one embodiment, the orthosis comprises a cushioning element 5 that also has a certain intrinsic stiffness. The cushioning element 5 has an appropriate shape and is disposed on the main part 1 so as to cover the carpometacarpal joints of the thumb. On FIGS. 2 to 4, the cushioning element has substantially the shape of a croissant with truncated ends (FIG. 8).

According to one embodiment, the cushioning element comprises a pad 5 made of a viscoelastic material, such as a cross-linked polymer gel, for example a non-adhesive cross-linked silicone gel that is fixed onto the face of the part 1.

Figure 7:
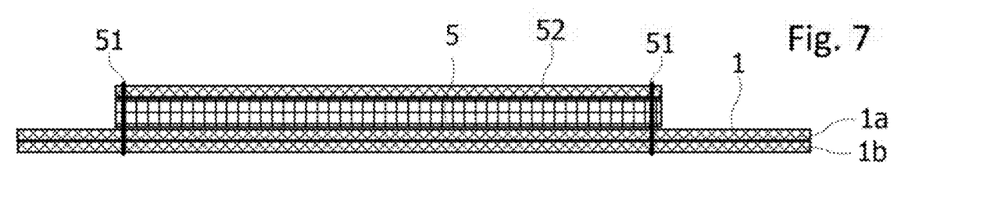
FIG. 7 is a cross-section of a portion of the orthosis, according to one embodiment.

FIG. 7 represents a portion of the orthosis onto which the pad 5 is fixed. As represented in FIG. 7, the pad 5 can be adhered onto a piece of fabric 52 that is fixed onto the inner face of the main part 1 of the orthosis by seams 51, the pad 5 being sandwiched between the main part 1 and the piece of fabric 52. FIG. 7 also shows the two layers 1a, 1b forming the main part 1.

According to one embodiment, the main part 1 can be made as a single piece 10 of which certain edges are assembled to form the orthosis. FIG. 8 represents the piece 10 laid flat, comprising the portions 2, 3, 4. The portions 2 and 4 have substantially the shape of a slightly curved strap, with a seam line 21, 41 at each end. The lines 21 are provided to be fixed one to the other to form the thumb sleeve 2. Similarly, the lines 41 are fixed to each other to form the hand palm sleeve 4. The portion 3 has a trapezoidal shape without any seam line. FIG. 8 also represents the pad 5 the greatest part of which is fixed onto the portion 4, and the remaining parts onto the portion 3, before making the seams 21, 41.

The piece 10 can be used indifferently to produce right- and left-hand orthoses. The hand for which the orthosis is intended is determined by the face onto which the pad 5 is fixed. Thus, the piece 10 represented in FIG. 8 is intended to produce a left-hand orthosis. The seams 21 and 41 are made by folding the piece 10 towards the outer face of the orthosis so as to superimpose the lines 21 to form the sleeve 2, and to superimpose the lines 41 to form the sleeve 4.

Figure 9A:
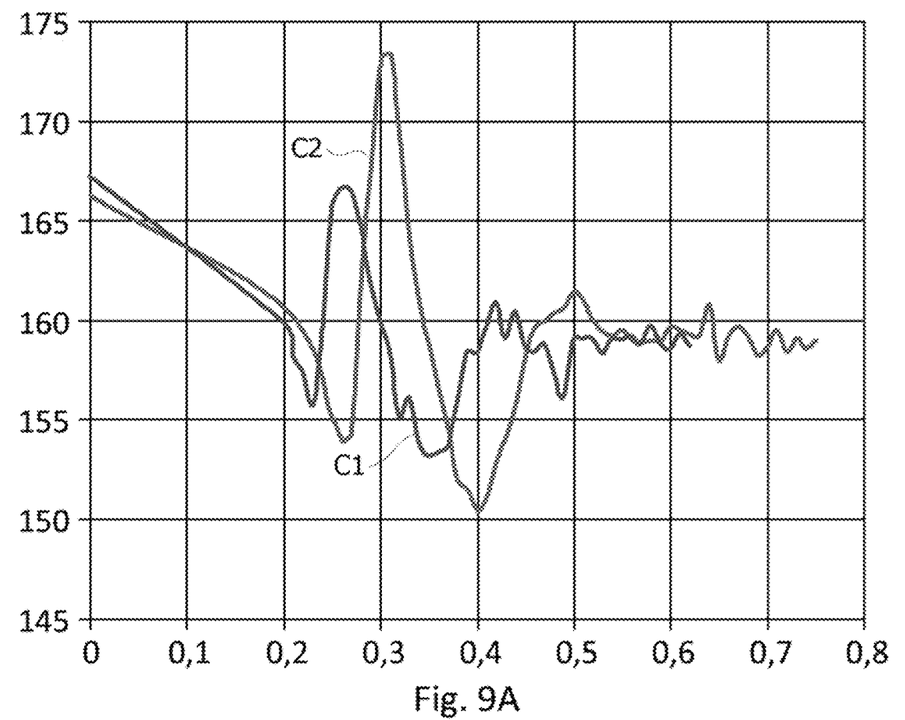
FIGS. 9A and 9B are curves showing the performances of the orthosis over time.
Figure 9B:
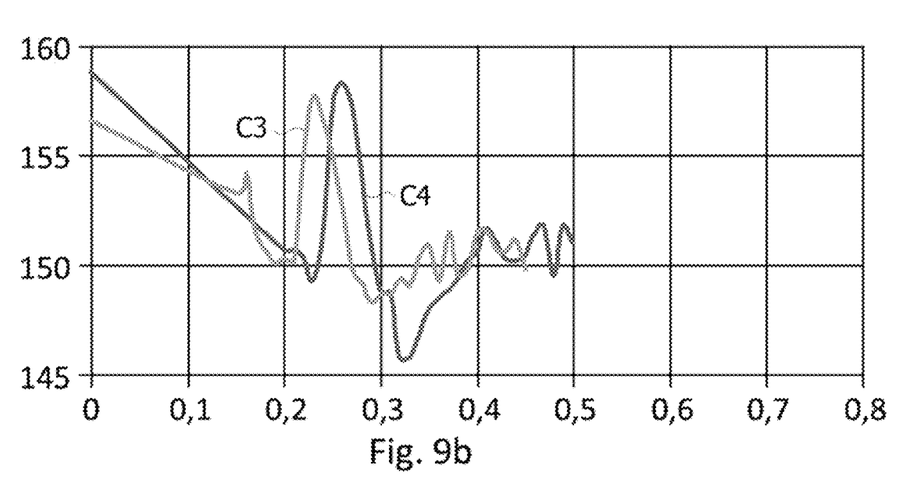

FIGS. 9A and 9B represent curves C1, C2, C3, C4 showing the performances of the orthosis. The curves C1 to C4 show the variations over time of the angle ABC formed by the carpometacarpal joints of the thumb when the hand falls onto a horizontal plane, muscles relaxed. The curves C1 and C3 correspond to a 5 cm fall, and the curves C2 and C4 to a 10 cm fall. The curves C1 and C2 on FIG. 9A show the case in which the hand is not wearing any orthosis and the curves C3 and C4 on FIG. 9B show the case in which the hand is wearing the orthosis as represented on FIGS. 2 to 4 and 8. According to the curve C1, the angle ABC reaches a peak at approximately 167° after the shock at the time 0.22 s, then varies between 154° and 161° in a cushioned manner. According to the curve C2, the angle ABC reaches a peak at approximately 173° after the shock at the time 0.25 s, then varies between 150° and 162° in a cushioned manner. According to the curve C3, the peak reached by the angle ABC is limited to approximately 157° (instead of 163° after the shock at the time 0.21 s, then varies between 148° and 152° in a cushioned manner. According to the curve C4, the peak reached by the angle ABC is limited to approximately 158° (instead of 173° after the shock at the time 0.22 s, then varies between 146° and 152° in a cushioned manner. The curves C1 to C4 show that the movements of the thumb around the joint MSA, resulting from the shock, have amplitudes that are attenuated thanks to the orthosis. It can also be seen that the oscillations resulting from the shock are shorter with the orthosis.

It shall be noted that these supporting and cushioning effects are obtained without the orthosis having to exert any retention forces in particular at the junction between the wrist and the hand. It is not therefore necessary for the orthosis to be fitted exactly to the hand of each individual to be relieved. The orthosis can thus be manufactured in a few standard sizes. Therefore, three to five standard sizes can be considered, given that 80% of cases can be covered with only three standard sizes.

It will be understood by those skilled in the art that the present invention is susceptible of various alternative embodiments and various applications. In particular, the invention is not limited to an orthosis comprising a cushioning pad. Indeed, the orthosis without the pad perfectly supports the carpometacarpal joints of the thumb of the joint in question. In addition, it can be seen that while the oscillations observed on FIG. 9B have lower amplitudes than on FIG. 9A, these oscillations are also shorter.

It is not necessary either to form the main part 1 using two layers of elastic fabric adhered to one another. Other materials can easily be found to give the main part 1 of the orthosis sufficient rigidity.

It is not necessary either for the sleeve of the thumb to cover the distal joint of the thumb. Indeed, the carpometacarpal joints are fully supported when the orthosis only covers the thumb up to the middle of the proximal phalanx. Furthermore, as the orthosis is only produced in a few standard sizes and is not custom-made, the portion of the thumb covered by the orthosis depends on each individual morphology.

The invention claimed is:

1. A hand orthosis for supporting a thumb of a hand, the hand orthosis comprising a sleeve that comprises:
   a first portion and a second portion both having a sleeve form, the first portion being adapted to fit a portion of the thumb extending to a fold area between the thumb and a palm of the hand, the second portion being assembled by a seam line and adapted to fit a wrist of the hand, and
   a third portion linking the first and second portions, shaped to envelop an area of the hand extending along a thumb metacarpal between a back and the palm of the hand, and comprising an opening to allow the palm of the hand to pass therethrough,
   wherein:
      the sleeve is made of elastic fabric,
      the sleeve is shaped so as not to cover the fold area between the thumb and the palm of the hand, and
      the sleeve has a Young's modulus of between 0.5 MPa and 1 MPa in a direction corresponding to a longitudinal axis of the first portion to configure the sleeve to bear the weight of the thumb, and to reduce amplitude and duration of involuntary movements without requiring significant additional muscular efforts to be exerted on the thumb for voluntary movements.

2. The hand orthosis according to claim 1, wherein the first portion is shaped to cover a joint between two phalanges of the thumb.

3. The hand orthosis according to claim 1, wherein the sleeve is made of two layers of the elastic fabric assembled by adhesion.

4. The hand orthosis according to claim 3, wherein each of the two layers is made from a fabric comprising between 75% and 85% by weight of polyamide and between 15% and 25% by weight of elastane.

5. The hand orthosis according to claim 3, wherein each of the two layers has a weight per unit area of 155 g/m$^2$, and/or a thickness of between 0.5 and 0.7 mm.

6. The hand orthosis according to claim 3, wherein each of the two layers has an elasticity of 85% to 115% in a warp direction of the elastic fabric and of 65% to 95% in a weft direction of the elastic fabric.

7. The hand orthosis according to claim 1, further comprising a pad made from a material capable of performing a cushioning function, the pad being fixed inside the second and third portions in an area of the sleeve adapted to cover a joint between the thumb metacarpal and the wrist.

8. The hand orthosis according to claim 7, wherein the pad is made from a cross-linked polymer gel.

9. The hand orthosis according to claim 7, wherein the pad has a thickness of between 0.4 and 1 mm.

10. The hand orthosis according to claim 7, wherein the pad is adhered onto an overlapping part made from an elastic fabric that is assembled with the sleeve by a seam, such that the pad is sandwiched between the sleeve and the overlapping part.

11. The hand orthosis according to claim 10, wherein the pad is sewn with the overlapping part onto the sleeve.

12. The hand orthosis according to claim 1, wherein the elastic fabric of the sleeve has a thickness of between 1 mm and 1.4 mm.

13. A hand orthosis for supporting a thumb of a hand, the hand orthosis comprising a sleeve that comprises:
  a first portion and a second portion both having a sleeve form, the first portion being adapted to fit a portion of the thumb extending to a fold area between the thumb and a palm of the hand, the second portion being assembled by a seam line and adapted to fit a wrist of the hand, and
  a third portion linking the first portion and the second portion, shaped to envelop an area of the hand extending along a thumb metacarpal between a back and the palm of the hand, and comprising an opening to allow the palm of the hand to pass therethrough,
  wherein:
    the sleeve is shaped so as not to cover the fold area between the thumb and the palm of the hand, and
    the sleeve is made of an elastic fabric comprising between 75% and 85% by weight of polyamide and between 15% and 25% by weight of elastane, such that the sleeve has a Young's modulus of between 0.5 MPa and 1 MPa in a direction corresponding to a longitudinal axis of the first portion, to configure the sleeve to bear the weight of the thumb, and to reduce amplitude and duration of involuntary movements without requiring significant additional muscular efforts to be exerted on the thumb for voluntary movements.

14. The hand orthosis according to claim 13, wherein the hand orthosis consists of the sleeve.

15. The hand orthosis according to claim 13, wherein the hand orthosis consists of the sleeve and a cushioning pad fixed to the sleeve.

16. The hand orthosis according to claim 13, wherein the hand orthosis is exclusively made of elastic material.

17. The hand orthosis according to claim 13, wherein the sleeve is made of two layers of the elastic fabric and the two layers are assembled by adhesion, and each of the two layers has an elasticity of 85% to 115% in a warp direction of the elastic fabric and of 65% to 95% in a weft direction of the elastic fabric.

18. A hand orthosis for supporting a thumb of a hand, the hand orthosis consisting of:
  a sleeve made of two layers of elastic fabric assembled by adhesion, the sleeve consisting of:
    a first portion and a second portion both having a sleeve form, the first portion being adapted to fit a portion of the thumb extending to a fold area between the thumb and a palm of the hand, the second portion being assembled by a seam line and adapted to fit a wrist of the hand, and
    a third portion linking the first and second portions, shaped to envelop an area of the hand extending along a thumb metacarpal between a back and the palm of the hand, and being open to allow the palm of the hand to pass therethrough,
  wherein:
    the sleeve is shaped so as not to cover the fold area between the thumb and the palm of the hand, and
    the sleeve has a Young's modulus of between 0.5 MPa and 1 MPa in a direction corresponding to a longitudinal axis of the first portion, to configure the sleeve to bear the weight of the thumb, and to reduce amplitude and duration of involuntary movements without requiring significant additional muscular efforts to be exerted on the thumb for voluntary movements.

* * * * *